United States Patent [19]

Speranza et al.

[11] Patent Number: 4,952,732
[45] Date of Patent: Aug. 28, 1990

[54] MANNICH CONDENSATES OF A SUBSTITUTED PHENOL AND AN ALKYLAMINE CONTAINING INTERNAL ALKOXY GROUPS

[75] Inventors: George P. Speranza, Austin; Robert A. Grigsby, Jr., Georgetown; Ernest L. Yeakey, Austin, all of Tex.

[73] Assignee: Texaco Inc., White Plains, N.Y.

[21] Appl. No.: 621,332

[22] Filed: Jun. 15, 1984

[51] Int. Cl.$^5$ .............................................. C07C 91/30
[52] U.S. Cl. ...................................... 564/390; 564/389
[58] Field of Search ................ 564/323, 388, 390, 505

[56] References Cited

U.S. PATENT DOCUMENTS

| | | | |
|---|---|---|---|
| 2,114,122 | 4/1938 | Bruson | 564/323 X |
| 2,304,729 | 12/1942 | Bruson | 564/323 X |
| 2,355,337 | 8/1944 | Spence | 564/505 X |
| 2,792,359 | 5/1957 | De Groote | 564/323 X |
| 2,802,820 | 8/1957 | Zech | 564/323 |
| 3,110,732 | 11/1963 | Speranza et al. | 564/505 |
| 3,161,682 | 12/1964 | Lesesne et al. | 564/505 X |
| 3,535,307 | 10/1970 | Moss et al. | 564/505 X |
| 3,580,952 | 5/1971 | Moschel | 564/505 X |
| 3,654,370 | 4/1972 | Yeakey | 564/505 X |
| 4,309,532 | 1/1982 | Cuscurida et al. | 564/475 X |
| 4,310,592 | 1/1982 | Schmitz | 428/288 |
| 4,332,595 | 6/1982 | Herbstman et al. | 564/505 X |
| 4,383,102 | 5/1983 | McDaniel et al. | 564/388 X |
| 4,392,867 | 7/1983 | Sung et al. | 564/505 X |
| 4,396,517 | 8/1983 | Gemmill, Jr. et al. | 252/51.5 |
| 4,499,264 | 2/1985 | McDaniel | 564/388 X |

OTHER PUBLICATIONS

"The Mannich Reaction", Org. Reactions 1, 303 (1942).

*Primary Examiner*—Robert V. Hines
*Attorney, Agent, or Firm*—Jack H. Park; Kenneth R. Priem; Carl G. Ries

[57] ABSTRACT

Products useful as surfactants, corrosion inhibitors, water repellent agents, paint adhesion promoters, etc. are prepared by reacting formaldehyde and a phenol with an alkyl amine containing internal propoxy or propoxy/ethoxy groups to thereby provide a corresponding Mannich condensate having a desired utility. The Mannich condensates may also be reacted with an alkylene oxide feed stock containing ethylene oxide or propylene oxide or 1,2-butylene oxide or a mixture thereof under conventional alkoxylation conditions to thereby provide a corresponding alkoxylated Mannich condensate having a utility which may be the same as or different from the utility of the initial Mannich condensate.

13 Claims, No Drawings

MANNICH CONDENSATES OF A SUBSTITUTED PHENOL AND AN ALKYLAMINE CONTAINING INTERNAL ALKOXY GROUPS

BACKGROUND OF THE INVENTION

1. Field of the Invention

This invention relates to initial Mannich condensates prepared from a phenol, formaldehyde and an alkylamine containing internal propoxy groups and, optionally, ethoxy groups and to alkoxylated derivatives of the initial Mannich condensates that also contain hydroxy-terminated alkoxide side chains depending from the amino group of the initial Mannich condensates; such initial and/or alkoxylated Mannich condensates being useful as surfactants, corrosion inhibitors, water repellent agents, paint adhesion promoters, and as intermediates for the preparation of surfactants with a wide range of cloud points and detergency.

More particularly, this invention relates to initial Mannich condensates that are prepared by reacting formaldehyde with phenol or a phenol substituted in the ortho or para position with a hydrocarbon group and also with an alkylamine wherein the alkyl group is separated from the amine group by one or more propoxy groups or by a mixture of ethoxy groups and propoxy groups to thereby provide a new class of chemicals having a wide variety of useful properties. The preparation of the Mannich condensates of the present invention is illustrated by the following equation:

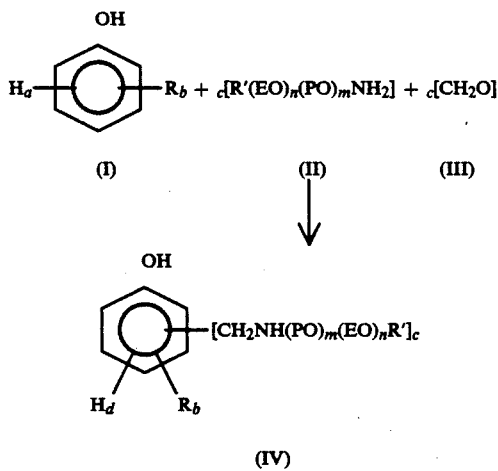

Where a equals 1 to 5, b equals 0 to 2, c equals 1 to 3, d equals 2 to 4; and Wherein: R represents an alkyl, an aryl and/or an alkaryl group; R' represents an aryl, arylalkyl or an alkyl group containing 1 to 20 carbon atoms; PO represents an oxypropyl group; EO represents an oxyethyl group; m is a number having a value of 1-50; and n is a number having a value of 0 to 50.

It is to be noted that in the equation given above, one phenolic hydrogen atom that is ortho or para to the phenolic hydroxyl group is replaced for each Mannich group that adds to the aromatic ring so that, in the final product, $H_d$ equals $H_a$ minus c.

This invention also relates to alkoxylated Mannich derivatives prepared from the initial Mannich condensates. The alkoxylated Mannich derivatives are prepared by reacting the initial Mannich condensate with an alkylene oxide feed stock comprising ethylene oxide, propylene oxide, 1,2-butylene oxide or a mixture thereof to thereby provide hydroxy-terminated groups derived from the alkylene oxide feed stock which are attached to the amino nitrogens of the initial Mannich condensate and to the phenolic hydroxyl group. In this fashion it is possible to convert an initial Mannich condensate having an initial utility to an alkoxylated derivative having an enhanced initial utility or a different utility. The formation of the alkoxylated Mannich condensates is illustrated by the following equation:

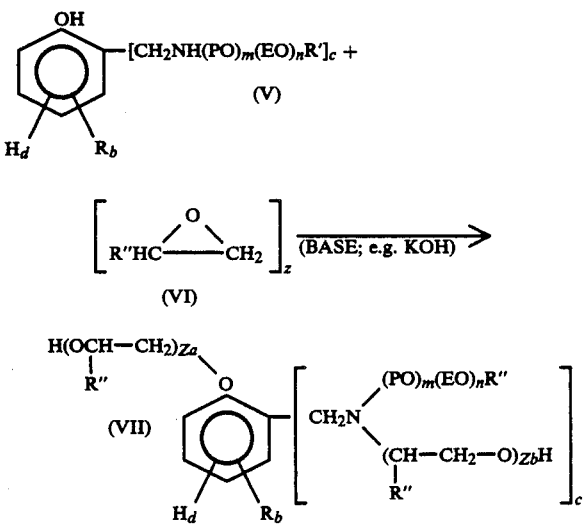

Wherein R" represents H, or methyl or ethyl; Z represents a positive integer having a value of 1 to 50; and $Z_a + Z_b$ equals Z.

2. Prior Art

The Mannich reaction is a well known reaction which has been extensively reviewed in the literature. See for example, "The Mannich Reaction", *Org. Reactions* 1, 303 (1942) and "Advances in the Chemistry of Mannich Bases", *Methods in Synthetic Organic Chemistry - Synthesis*, Academic Press, pp. 703–775, 1973.

A representative patent illustrating the manner in which the Mannich reaction can be utilized to prepare useful products is Schmitz U.S. Pat. No. 4,310,592. Schmitz reacts an aliphatic amine and formaldehyde with phenol to provide an ortho substituted Mannich base condensate which is useful for increasing the water repellent properties of materials treated therewith.

SUMMARY OF INVENTION

It has been surprisingly discovered in accordance with the present invention that a new class of Mannich condensates having wide utility are provided when a phenolic feedstock (as hereinafter described) is reacted with formaldehyde and a polyoxypropylene alkylamine (as hereinafter described). The initial Mannich condensate products of the present invention have unique utility in that the hydrophobicity and the hydrophilicity can be controlled with precision by the appropriate choice of the starting materials. As a consequence, the initial Mannich condensate products of the present invention can be either water soluble or oil soluble and are useful, for example, as corrosion inhibitors, water repellent agents, paint adhesion promoters, and also as intermediates for the preparation of surfactants having a wide range of cloud points and detergent values and also as intermediates for the preparation of polyols useful in the manufacture of polyurethane foam.

The alkoxylated derivatives of the initial Mannich condensates also have utility as corrosion inhibitors, surfactants, water repellent agents, paint adhesion promoters, etc. An advantage that is obtained in making and using the alkoxylated derivatives is the even greater control that can be exercised over the relative hydrophobicity of the products that can be obtained by using the alkylene oxide feed stock to enhance or even reverse the hydrophobiscity of the initial product.

Thus, hydrophobicity can be enhanced by the use of propylene oxide and/or 1,2-butylene oxide, whereas it can be reduced by the use of ethylene oxide. By way of illustration, an initial Mannich condensate that is a water-insoluble corrosion inhibitor can be converted to a water-soluble surfactant through the use of an alkylene oxide feed stock consisting essentially of ethylene oxide as shown by the following equation wherein the letters have the meaning given above.

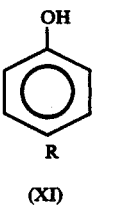

(XI)

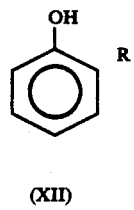

(XII)

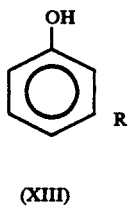

(XIII)

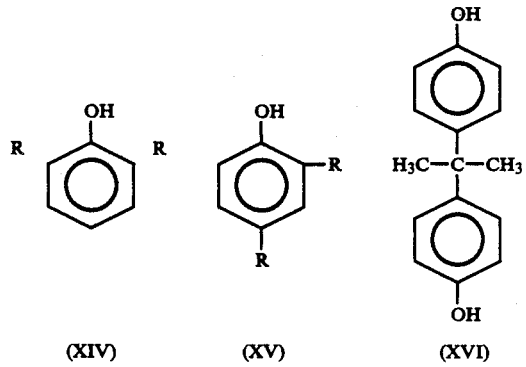

(XIV)  (XV)  (XVI)

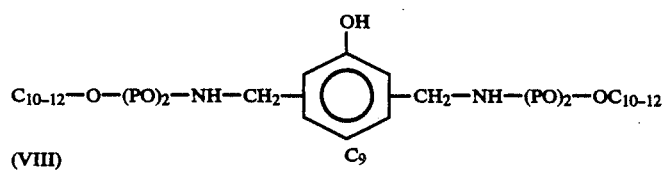

(VIII)

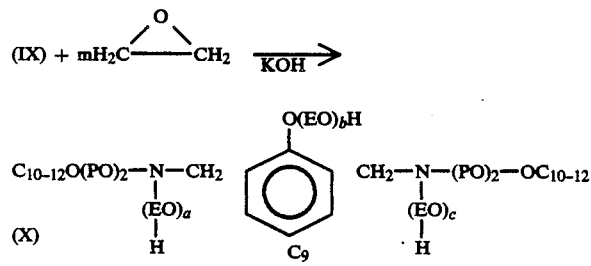

(X)

where $a + b + c = m$

STARTING MATERIALS

The Formaldehyde

The formaldehyde may be employed in any of its conventional forms. Thus it may be, and is preferably, used in the form of an aqueous solution of formaldehyde such as "formalin", in "inhibited" methanol solution, as paraformaldehydem, or as trioxane.

Phenol Compounds

The phenolic compounds to be used as feedstocks in accordance with the present invention are the mono- and disubstituted phenols such as those shown in formulae XI through XVI.

The group with which the phenol is substituted may be a straight chain alkyl group such as an alkyl group containing from 1 to 20 carbon atoms, a branch chain alkyl group such as an isopropyl group, a tertiary butyl group, a nonyl group or a dodecyl group derived from the polymerization of propylene, etc. It may also be a phenyl group or a substituted phenyl group or an alkaryl group, for example, as bisphenol "A" shown in Formula XVI.

Representative examples of compounds having Formula XI given above include the compounds such as p-methylphenol, p-ethylphenol, p-n-propylphenol, p-isopropylphenol, n-butyl-, isobutyl-, or tert. butyl- para substituted phenols, corresponding amylphenols, p-hexylphenol, p-nonylphenol, p-dodecylphenol, p-pentadecylphenol, p-octadecylphenol, etc. The phenol may also be substituted with a phenyl group or, as shown in Formula XVI, with an alkylaryl group.

Examples of ortho substituted phenols that may be used include compounds such as 2,6-di-t-butylphenol, 2-methyl-6-t-butylphenol, 2,6-di-ethylphenol, 2,6-diisopropylphenol, ortho-cresol, ortho-ethylphenol, ortho-nonylphenol, 2,6-di-nonylphenol, etc.

The Primary Amine

The amine starting material to be used in accordance with the present invention may suitably be an amine having the formula given below:

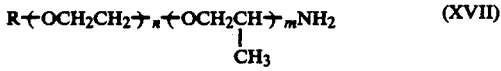

wherein: R represents an alkyl, an aryl, or an alkaryl group.

When the amine is composed primarily of propylene oxide adducts, the amine and the resultant Mannich condensate will be oil soluble. Conversely, when the amine contains a high proportion of ethoxy groups, the amine and the corresponding Mannich condensate will be water soluble. Examples of suitable primary amine starting materials are given in Table I.

TABLE I

| Primary Amine Starting Materials | | | |
|---|---|---|---|
| (XVIII) | R-(EO/PO)$_m$-NH$_2$ | | |
| Wherein: | | | |
| Compound Code | R | Mol. Wt. of Formula (XVI) | Mols PO/EO |
| M-300 | n-C$_{10}$–C$_{16}$— | 300 | 2/0 |
| M-360 | n-C$_4$H$_9$— | 360 | 2/3 |
| M-600 | CH$_3$— | 600 | 9/1 |
| M-1000 | CH$_3$— | 1,000 | 3/19 |
| M-2005 | CH$_3$— | 2,000 | 32/3 |
| M-2070 | CH$_3$— | 2,000 | 10/32 |

It will be observed that the amines having the code designations M-300, M-600 and M-2005 are composed principally or exclusively of propoxy groups in the intermediate chain. These products and the resultant Mannich condensates formed therefrom are oil soluble. Likewise it will be noted that the amines designated by the codes M-360, M-1000 and M-2070 contain significantly large quantities of ethylene oxide as compared to the quantity of propylene oxide that was used in the manufacture of the amine. These products, containing a predominating amount of ethoxy groups will be water soluble.

Preparation of the Initial Mannich Condensate

The relative quantities of phenolic starting material, formaldehyde and amine will be determined by the nature of the final product that is desired. If a monosubstituted Mannich condensate is desired, then the phenolic starting material, the amine starting material and the formaldehyde should be used in approximately equimolar amounts. As another example, if a bis Mannich condensate is desired, then about 2 moles of formaldehyde and about 2 moles of amine should be used per mole of phenolic starting material.

The reaction is preferably conducted at atmospheric pressure although subatmospheric pressures and/or superatmospheric pressures may be used if desired.

The reaction is normally conducted within a temperature range of about 80° to about 120° C for the lower molecular weight products wherein the amine of Formula XVIII has an average molecular weight of about 250 to about 500.

However, when higher molecular weight amines are used, such as those having molecular weights within the range of about 500 to about 2000, it is necessary to use higher temperatures and/or pressures, such as temperatures within the range of about 100° to about 150° C. and pressures within the range of about 1 atm. to about 50 atm.

Preparation of the Alkoxylated Derivatives

The initial Mannich condensates are alkoxylated in accordance with the present invention to provide the alkoxylated derivatives. The alkoxylation reaction can be conducted in the conventional manner in conventional equipment under basic conditions. However, since the initial Mannich condensates contain basic nitrogen, they are self-catalyzing insofar as alkoxylation is concerned up to the addition of about 5 mols of alkylene oxide per mol of Mannich condensate. If larger amounts of alkylene oxide are to be added to the initial Mannich condensate, it is necessary to increase the basicity of the alkoxylation medium in the manner known to those skilled in the art by adding a conventional basic catalyst, such as an alkali metal hydroxide (e.g., sodium or potassium hydroxide), an alkaline earth metal (e.g., calcium, barium or magnesium) hydroxide. Alkoxylation conditions to be used are conventional alkoxylation conditions including a temperature of about 80° to about 140° C. and a pressure of about 15 to about 250 psig.

DETAILED DESCRIPTION OF PREFERRED EMBODIMENTS OF THE PRESENT INVENTION

Initial Mannich Condensates

The preparation and use of the Mannich condensates of the present invention is further illustrated by the following specific examples which are given by way of illustration and which are not intended as limitations on the scope of this invention.

EXAMPLE 1

This example illustrates the technique used in most runs. To a 500 ml. three necked flask equipped with a stirrer, and thermometer and a simple take off joint was added 39.33 g of nonylphenol (0.165 moles), 100 g of Jeffamine$^R$ M-300 amine (0.33 moles) and 26.8 g of aqueous 37% formaldehyde (0.33 moles). The reactants were heated for four hours at 90–99° C. Then the product was heated at 150° C. and 10 mm. pressure to remove the water. The product weighed 142.3 g and analyzed as 3.3 meq/g of total acetylatables, 2.48 total amine, 2.46 meq/g secondary and tertiary amine of which 0.24 was tertiary (Table II, run 5757-85).

In some cases, determination of the secondary and tertiary amine content was questionable because the end points were not too clear. We then asked for an interpretation by NMR on the degree of substitution on the phenolic ring. It was the NMR analysis that permitted us to understand the reaction far better.

EXAMPLE 2

In this example, Jeffamine amine M-600, nonylphenol and formaldehyde were heated as described above. Monoring substitution was greater than no substitution which was greater than disubstitution (Table II, run 5757-91). Now compare this run to 5773-41 (Table III) where the reaction was run in a closed vessel at 110150° C. under more forcing conditions. Disubstitution is much greater than monosubstitution which is greater than no ortho substitution. (See following experiments).

EXAMPLE 3

The course of our work became clearer. As the molecular weight of the Jeffamine amine product became higher more strenuous reaction conditions were needed. In 5763-32 (Table II) two moles of M-1000 were reacted with two moles formaldehyde and one mole of nonylphenol for 6.75 hours at 90–106° C. and atmospheric pressure. Mono substitution was approximately equal to no substitution which was greater than disubstitution. In run 5573-40 (Table III) when the same reagents in the same molar ratios were heated at 110–150° C. in an autoclave we found that disubstitution was greater than or equal to monosubstitution which was greater than no substitution.

5812-16 (Table III). In this case we first add one mole of M-1000 (1 hydrophilic segment) and one mole of formaldehyde to nonylphenol; next one mole M-360 was added along with a mole of formaldehyde. The first part of the reaction was carried out at 150° C. for four hours as was the second part. The reactants chosen were not ideal to make an optimum surfactant, but the broad range of new products that can be prepared by our invention is demonstrated.

Tables II and III show some cloud point data and solubility data and foam evaluations for water soluble products. Four stars denotes a good foamer. Foaming properties are presented on a graduated basis.

TABLE II

Mannich Reactions

| | Run No. | | | | | | | | | | |
|---|---|---|---|---|---|---|---|---|---|---|---|
| | 5757-85 | 5757-90 | 5757-91 | 5757-93 | 5757-95 | 5757-97 | 5763-29 | 5763-30 | 5763-31 | 5763-32 | 5763-33 |
| Cpd. Code | M300 | M360 | M600 | M1000 | M300 | M360 | M300 | M360 | M600 | M1000 | M1000 |
| g. | 100. | 100 | 100. | 100. | 150. | 100. | 191.5 | 230 | 109.9 | 136.4 | 159.6 |
| m. | 0.33 | 0.278 | .167 | 0.10 | 0.50 | 0.277 | 0.64 | 0.64 | 0.08 | 0.136 | 0.16 |
| phenol | C-9 | C-9 | C-9 | C-9 | — | C-12 | — | — | C-9 | C-9 | — |
| g. | 39.3 | 32.8 | 19.7 | 11.8 | 42.7 | 65.9 | 20. | 20. | 20. | 15. | 5. |
| m. | 0.165 | 0.139 | 0.083 | 0.05 | 0.454 | 0.252 | 0.21 | 0.21 | 0.09 | 0.068 | 0.05 |
| $H_2CO$ m. | 0.33 | 0.278 | 0.167 | 0.10 | 0.5 | 0.277 | 0.64 | 0.64 | 0.08 | 0.136 | 0.16 |
| Time, hrs. | 4 | 4 | 4 | 4 | 5 | 1 | 5.5 | 5.5 | 8.0 | 6.75 | 2.5 |
| Temp. 0° C. | 90–99 | 90–99 | 90–96 | 90–94 | 90 | 90–96 | 90 | 90–99 | 90–94 | 90–106 | 90–93 |
| Vac. | Y | Y | Y | Y | Y | Y | Y | Y | Y | Y | Y |
| max.T 0° C. | 150 | 150 | 156 | 150 | 140 | 140 | 180 | 160 | 180 | 180 | 175 |
| Total Acetylatables | 3.3 | 3.03 | 1.96 | 1.27 | 4.73 | 2.90 | | | | | |
| Tot. Amine meq/g | 2.48 | 1.95 | 1.45 | 0.75 | 2.70 | 1.57 | 3.1 | 2.35 | 1.43 | 0.71 | 0.72 |
| 2 & 3 meq/g | 2.46 | 1.93 | 1.44 | 0.73 | 2.76 | 1.56 | 3.1 | 2.38 | 1.45 | 0.71 | 0.71 |
| 3 meq/g | 0.24 | 0.21 | 0.07 | 0.03 | 0.34 | 0.23 | 0.25 | 0.3 | 0.14 | 0.18 | 0.08 |
| Cloud Pt. °C. | | | | | | | | | | 85 | 85 |

NMR Data - Number of $CH_2$—NH—R Groups Substituted on the Ring
Relative Molar Ratio

| | | | | | 0>1 | 0=1 | 2>>1 | 2>1 | 2>>1 | 1=0 | 0>>1 |
|---|---|---|---|---|---|---|---|---|---|---|---|
| | 2>1>0 | 2>1>0 | 1>0>2 | 0>1>2 | >>2 | >>2 | >0 | >0 | >0 | >>2 | >2 |

Water Solubility Data

| | | | | | | | | | | | |
|---|---|---|---|---|---|---|---|---|---|---|---|
| Isop. | + | + | + | + | + | + | + | + | + | + | + |
| Tol | + | + | + | + | + | + | + | + | + | + | + |
| Water | — | — | — | + | — | — | — | — | — | + | + |
| Foams | | | | ++++ | | | | | | +++ | + |

EXAMPLE 4

The wide variety of products that can be made with the techniques of our invention can be described in run

TABLE III

Mannich Reactions

| | Run No. | | | | | | | | | |
|---|---|---|---|---|---|---|---|---|---|---|
| | 5763-51 | 5763-52 | 5763-53 | 5763-54 | 5763-55 | 5763-57 | 5773-34 | 5773-40 | 5773-41 | 5812-16 |
| Cpd. Code | M-1000 | M-1000 | M-600 | M-1000 | M-360 | M-1000 | M-1000 | M-1000 | M-600 | M1000/M360 |
| g. | 153.2 | 606.9 | 700. | 750 | 650 | 125.0 | 200 | 1000 | 1000 | 318/115 |
| m. | 0.153 | 0.609 | 1.167 | 0.75 | 1.80 | 0.125 | 0.2 | 1.0 | 1.66 | 0.32/0.32 |
| phenol | C-12 | C-9(2) | C-9 | C-9 | C-9 | C-9 | C-9 | C-9 | C-9 | C-9 |
| g. | 20. | 200 | 128.3 | 82.5 | 198.6 | 25.0 | 22 | 110 | 183.3 | 70.0 |
| m. | 0.076 | 0.578 | 0.583 | 0.375 | 0.902 | 0.114 | 0.1 | 0.5 | 0.833 | 0.32 |
| $H_2CO$ m. | 0.153 | 0.609 | 1.167 | 0.75 | 1.80 | 0.125 | 0.2 | 1.23 | 1.668 | 0.64 |
| Time, hrs. | 3. | 4. | 4. | 4.5 | 3.4 | 3.0 | 6 | 5 | 5 | |
| Rx. T °C. | 90 | 90 | 93 | 92 | 92 | 95 | 90 | 110–150 | 110–150 | |
| Vac. | Y | Y | Y | Y | Y | Y | Y | Y | Y | |
| Max. T °C. | 150 | 150 | 145 | 145 | 150 | 140 | 145 | 140 | 140 | |
| OH # | | | | | | | | | | |
| T.Act. meq/g | | | | | | 1.38 | | | | |
| Tot. amine meq/g | 0.73 | 0.6 | 1.44 | 0.70 | 1.99 | 1.27 | 0.7 | 0.66 | 1.43 | 1.08 |
| 2 & 3 meq/g | 0.1 | 0.05 | 0.34 | 0.1 | 0.04 | 0.65 | 0.1 | 0.25 | 0.48 | 0.29 |
| 3 meq/g | 0.05 | 0.03 | 0.08 | 0.04 | 0.24 | 0.11 | 0.03 | 0.15 | 0.17 | 0.22 H.P. Run* |
| Cld.Pt. °C. | 81 | | | 82 | | 74 | 84 | 85 | | 74 |

NMR Data - Number of $CH_2$—NH—R Groups Substituted on the Ring
Relative Molar Ratio TABLE III-continued

| | Mannich Reactions Run No. | | | | | | | | | |
|---|---|---|---|---|---|---|---|---|---|---|
| | 5763-51 | 5763-52 | 5763-53 | 5763-54 | 5763-55 | 5763-57 | 5773-34 | 5773-40 | 5773-41 | 5812-16 |
| | 0>?>1>>2 | | 1=2=0 | 0>1 >>2 | 2>>1>0 | 1>2>>0 | 0>1 >>2 | 2>1>0 H.P. Run* | 2>>>1 >0 H.P. Run* | |
| Water Solubility Data | | | | | | | | | | |
| Iso. | + | + | + | + | + | + | + | + | + | + |
| Tol | + | + | + | + | + | + | + | + | + | + |
| Water | + | − | − | + | − | + | + | + | − | + |
| Foams | +++ | | | +++ | | +++ | ++++ | ++++ | | +++ |

*Runs made in closed autoclavs under pressure

EXAMPLE 5

As has been indicated earlier, the products of the present invention have utility as corrosion inhibitors.

As an example of the use of a product of the present invention as a water soluble corrosion inhibitor, a Mannich condensate was prepared from equimolar proportions of amine M-1000 and formaldehyde and nonylphenol. In order to test for corrosivity, 60 g of deionized water and 1.2 g of the Mannich condensate were added to a 150 ml. beaker, a 1.5"×0.5"×0.1" mild steel coupon was placed upright in the beaker with about ½" of the coupon extending above the liquid surface. Even one hour later, dramatic results were obtained, as is shown from attached Table IV.

TABLE IV

| Corrosion Inhibition | | | |
|---|---|---|---|
| Sample No. | Product Description[1] | Time Expired | Comments |
| Control | Water + coupon | 77 minutes | Rust streakes at surface and below surface |
| | | 17 hours | Rust at surface and below surface |
| 5773-40 | M-1000 | 77 minutes | No rust streakes below surface - One spot at surface |
| | | 17 hours | Spotted with some rust |

EXAMPLE 6

As an illustration of the utility of the initial Mannich condensates of the present invention as corrosion inhibitors wherein the Mannich condensates are oil soluble, a series of Mannich condensates were prepared and tested for their effect in passivating mild steel. In this test, two Mannich condensates were used. One Mannich condensate was prepared by reacting equimolar amounts of nonylphenol and formaldehyde with amine M-360. The other product was a Mannich condensate prepared by reacting equimolar amounts of nonylphenol and formaldehyde with amine M-600 in the manner described above in the examples.

In testing for corrosivity, in each test, 25 cc of cyclohexane and 1 g of Austin tap water were added to a closed top jar. A coupon having dimensions of 1.5"×0.5"X 0.1" and prepared for mild steel was then positioned in the jar and the jar was tilted so that a portion of the coupon was in the water layer and a portion of the coupon was in the cyclohexane layer. 0.5 g of additive to be tested was added and the two layers were shaken. The results that were obtained are shown in Table V. As can be seen from Table V, the Mannich condensates of the present invention were once again effective in inhibiting rust.

TABLE V

| Product Description | Results |
|---|---|
| 5757-90 | Coupon shows no rust |
| M-360 | spots; nice surface |
| 5773-41 | Coupon shows no rust |
| M-600 | spots; nice surface |

EXAMPLE 7

As a further illustration of the products that can be obtained in accordance with the present invention, a series of Mannich condensates were prepared wherein the phenol that was used was bisphenol A. Amines having the code designation M-360, M-300, M-600 and M-1000 were used. In one experiment a mixture of M-1000 and M-300 was used.

The reaction procedure that was utilized was as follows: In a nitrogen filled two liter flask with three necks, 600 g of Jeffamine amine M-300 and 228 g of bisphenol A were added together and heated at 100° C., with stirring, for half an hour until the bisphenol A dissolved. The reaction mixture was cooled to 10° C. and 162.0 g of formalin (37% formaldehyde) was slowly added to the reaction mixture. After all of the formalin was added, the reaction temperature had reached 30° C. The reaction temperature was then held at 30° C. for half an hour. The temperature of the reaction was then increased to 100° C. to remove the water from the product. After all of the water was removed from the reaction mixture at 100° C., a water aspirator vacuum was connected to the reaction vessel. The reaction was then kept under vacuum for six hours at 100° C. Then, the reaction was allowed to cool to room temperature and the vacuum was replaced with a nitrogen atmosphere. The yellow product was then weighed, 849.3 g, and analyzed.

The products thus produced may be characterized by the following formula:

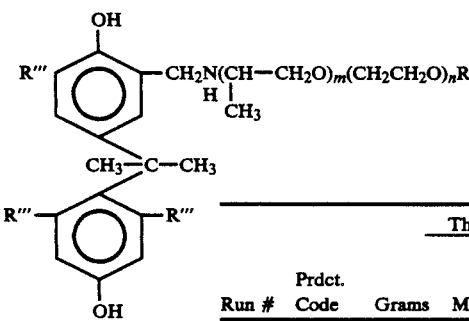

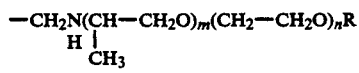

(XIX)

$$-CH_2N(CH-CH_2O)_m(CH_2-CH_2O)_nR \quad\quad (XX)$$
$$\phantom{-CH_2N(}H\phantom{H}|$$
$$\phantom{-CH_2N(H}CH_3$$

The results that were obtained are summarized in Table VI.

TABLE VI

The Reaction of Jeffamine Amines M-Series with Bisphenol A

| Run # | Prdct. Code | Grams | Moles | Bisphenol A Moles | Formalin | Temp. °C. | Time, hrs. | Total Amine meq/g | Tert. Amine meq/g | OH # | Descrip. |
|---|---|---|---|---|---|---|---|---|---|---|---|
| 5825-50 | M-300 | 600 | 2.0 | 1.0 | 2.0 | 110 | 7 | 2.51 | 0.30 | 134 | Yel Liq |
| 5825-51 | M-360 | 631.6 | 1.75 | 0.877 | 1.75 | 110 | 6 | 1.95 | 0.32 | 203 | Yel Liq |
| 5825-52 | M-600 | 526.3 | 0.877 | 0.439 | 0.877 | 110 | 6.5 | 1.42 | 0.17 | 141 | Gold Liq |
| 5825-53 | M-1000 | 75.0 | 0.66 | 0.33 | 0.66 | 110 | 10 | 0.71 | 0.19 | 88 | Yel Solid |
| 5825-54 | M-1000/300 | 438.6 131.6 | 0.44 0.44 | 0.44 | 0.88 | 110 | 10.5 | 1.17 | 0.23 | 134 | Yel Solid | wherein R''' represents hydrogen or a group having the formula:

EXAMPLE 8

To a one liter stirred autoclave was added 300 grams of the Mannich reaction from nonyl phenol and Jeffamine M-360 amine (5463-55, Table III). The clave was closed and the contents flushed with nitrogen. Ethylene oxide was added and the reaction held at 150° C. A total of 54 ml. of ethylene oxide was added, which represented by analysis 4.5 mols of oxide per aromatic ring. The hydroxyl number was 111 and the product was soluble in isopropanol and toluene and insoluble in water. This and other examples are shown in Tables VII and VIII.

TABLE VII

Reaction of Ethylene Oxide or Propylene Oxide with Initial Mannich Products

| | Run # | | | | | |
|---|---|---|---|---|---|---|
| | 5763-70 | 5763-75 | 5763-99 | 5773-35 | 5773-36 | 5773-75 |
| Phenol used | C-9 | C-9 | C-9 | — | C-9 | C-9 |
| M product used in Mannich Rx | M-360 | M-600 | M-360 | M-300 | M-600 | M-600 |
| g. of Mannich | 300 | 300 | 302.9 | 188 | 200 | 200 |
| Base Cat. | N | N | Y | Y | Y | Y |
| % KOH | | | 1.5 | 1.3 | 1.7 | 2.0 |
| Neutralized | N | N | Y | Y | Y | Y H2SO4 |
| mL of EO | 54 | 50 | 300 | 190 | 200 | |
| mL of PO | | | | | | 300 |
| Amount | | | 550.1 | | | 379.2 |
| Cloud Point °C. | — | — | 66 | 77 | 79 | — |
| OH # | 111 | 113 | 86.2 | 132 | 62.7 | 67.1 |
| T Amine | | | | | 0.72 | |
| 2 & 3 Amine | | | | | 0.45 | |
| 3 Amine | | | | | 0.43 | |
| PH | | | | | | 8.8 |
| NMR Results - Ring Substitution | | | 2>1>>>0 2 only | | Lost 1 Ortho | |
| NMR - Increased EO or PO Units | 4.5//AROM | >10% | 19.5//AROM | 22 | 22./AROM | 25 PO//M-600 |
| Solubility Data | | | | | | |
| Isopropanol | + | + | + | + | + | + |
| Toluene | + | + | + | + | + | + |
| Water | PPT | +/− | + | + | + | − |
| Foam | — | — | +++ | ++ | ++ | — |
| Mannich Reaction Came From | 5763-55 | 5763-53 | 5763-55 | 5763-29 | 5763-53 | 5773-41 |

TABLE VIII

Reaction of Ethylene Oxide or Propylene Oxide with Initial Mannich Products

| | Run # | | | | |
|---|---|---|---|---|---|
| | 5788-31 | 5788-32 | 5788-38 | 5812-22 | 5812-23 |
| Phenol used | C-9 | C-9 | C-9 | — | C-6 |
| M product used in Mannich Rx | M-1000 | M-1000 | M-600 | M-1000 | M-360 |
| g. of Mannich | 200 | 200 | 200 | 250 | 198.3 |
| Base Cat. | Y | Y | Y | Y | Y |
| % KOH | 2.0 | 2.0 | 2.0 | 2.0 | 1.0 NaOH |
| Neutralized | Y OXY | Y H2SO4 | Y OXY | H2SO4 | GLYC |
| mL of EO | | 200 | 200 | | 200 |
| mL of PO | 300 | | | 250 | |
| Amount | 333.3 | 294.9 | 368.3 | 438.4 | 375 |
| Cloud Point °C. | 34 | >100 | 74 | 46 | 70 |
| OH # | | 30.2 | 65.7 | | |
| T Amine | | 3.2 | 0.76 | 0.34 | |
| 2 & 3 Amine | | 0.17 | 0.43 | 0.24 | |
| 3 Amine | | 0.04 | 0.45 | 0.17 | |
| PH | | | 11.6 | 8.6 | 12.9 |
| NMR - Increased EO or PO Units | 23 PO/ /M-1000 | 20 EO/ /M-1000 | 33 EO/ /Aromatic | | |
| Solubility Data | | | | | |
| Isopropanol | + | — | + | + | + |
| Toluene | +/— | + | + | + | + |
| Water | + | + | + | + | + |
| Foam | + | ++ | + | ++ | +++ |
| Mannich Reaction Came From | 5763-54 | 5763-54 | 5773-41 | 5773-40 | 5763-55 |

In general, when ethylene oxide was the reactant and a base catalyst was used, the addition was made at 100° C. When propylene oxide was used with a base catalyst the reaction was run at 120° C. Those skilled in the art will understand this phase of the operation. Those skilled in the art will readily appreciate the versatility of this invention. We can start with water insoluble products and prepare water soluble products which are useful in many applications, such as detergents. Likewise, we can initiate the reaction from water soluble products and after the addition of propyl ene oxide prepare water insoluble products which have numerous uses, i.e., corrosion inhibitors, surfactants, etc.

The foregoing examples are given by way of illustration only and are not intended as limitations on the scope of this invention as defined by the appended claims.

What is claimed is:

1. A compound having the formula:

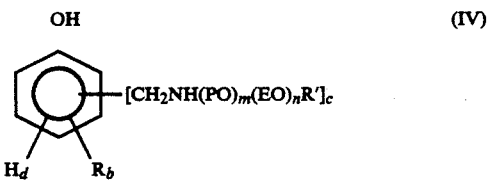

(IV)

where b equals 0 to 2, c equals 1 to 2, d equals 2 to 4; and wherein:

R represents an alkyl group containing 1 to 20 carbon atoms, and when b equals 1 and is in the para position, may also represent a group having the formula:

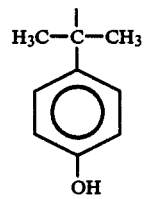

R' represents an alkyl group containing 1 to 20 carbon atoms;
PO represents an oxypropyl group;
EO represents an oxyethyl group;
m is a number having a value of 1–50; and
n is a number having a value of 0 to 50.

2. A compound as in claim 1 wherein d equals 3, b equals 1 and c equals 1.
3. A compound as in claim 1 wherein d equals 4, b equals 0 and c equals 1.
4. A compound as in claim 1 wherein d equals 2, b equals 0 and c equals 3.
5. A compound as in claim 1 wherein d equals 2, b equals 1 and c equals 2.
6. A compound as in claim 1 wherein R represents an alkyl group having 1 to 20 carbon atoms.
7. A compound as in claim 1 wherein R' represents an alkyl group having 8 to 18 carbon atoms, n equals 0 and m equals 2.
8. A compound as in claim 7 wherein R' represents a methoxyethyl group, n equals 0 and m equals 9.
9. A compound as in claim 1 wherein b is 1 and is in the para position and R represents a group having the formula:

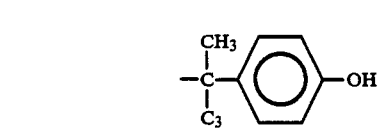

10. A compound as in claim 9 wherein R' represents a $C_{8-18}$ alkyl group, n equals 0 and m equals 2.
11. A compound as in claim 9 wherein R' represents a butyl group, n equals 3 and m equals 2.
12. A compound as in claim 9 wherein R' represents a methoxyethyl group, n equals 18 and m equals 3.
13. A compound as in claim 9 wherein R' represents a methoxyethyl group, n equals 0 and m equals 9.

* * * * *